US006521271B1

(12) United States Patent
Phan

(10) Patent No.: US 6,521,271 B1
(45) Date of Patent: Feb. 18, 2003

(54) COMPOSITIONS AND METHODS OF TREATMENT FOR SKIN CONDITIONS USING EXTRACTS OF TURMERIC

(75) Inventor: Dung Phan, 1101 Saddlewood Dr., San Jose, CA (US) 95121

(73) Assignee: Dung Phan, San Jose, CA (US)

( * ) Notice: Subject to any disclaimer, the term of this patent is extended or adjusted under 35 U.S.C. 154(b) by 0 days.

(21) Appl. No.: 09/890,941

(22) PCT Filed: Aug. 15, 2000

(86) PCT No.: PCT/US00/40641

§ 371 (c)(1),
(2), (4) Date: Aug. 6, 2001

(87) PCT Pub. No.: WO01/12130

PCT Pub. Date: Feb. 22, 2001

Related U.S. Application Data

(60) Provisional application No. 60/149,219, filed on Aug. 16, 1999.

(51) Int. Cl.$^7$ .......................... A61K 7/44; A61K 31/60; A61K 31/19; A61K 31/045
(52) U.S. Cl. ........................... 424/756; 424/59; 424/60; 424/62; 514/165; 514/557; 514/729; 514/730; 514/731; 514/732
(58) Field of Search ........................ 424/756, 59, 60, 424/62; 514/557, 165, 729, 730, 731, 732

(56) References Cited

U.S. PATENT DOCUMENTS

| | | | | |
|---|---|---|---|---|
| 5,152,983 | A | * | 10/1992 | Nambudiry et al. |
| 5,760,079 | A | * | 6/1998 | Shaffer et al. |
| 5,861,415 | A | * | 1/1999 | Majeed et al. |
| 5,935,596 | A | * | 8/1999 | Crotty et al. |
| 6,277,881 | B1 | * | 8/2001 | Santhanam et al. |
| 6,284,802 | B1 | * | 9/2001 | Bissett et al. |
| 6,294,186 | B1 | * | 9/2001 | Beerse et al. |
| 6,306,383 | B1 | * | 10/2001 | Crandall |

OTHER PUBLICATIONS

Ammon et al. (1993) "Mechanism of antiinflammatory actions of curcumine and boswellic acids." *J. Ethopharmacol* 38:113–119.
Azuine and Bhide (1992) "Chemopreventive Effect of Turmeric Against Stomach and Skin Tumors Induced by chemical Carcinogens in Swiss Mice." *Nutrition and Cancer* 17:77–83.
Charles and Charles (1992) The Use of Efficacy of Azadirachta Indica ADR ('NEEM') and Curcuma Longa ('Turmeric') In Scabies. *Tropical and Geographical Medicine* 44:178–181.
Conney et al. (1991) "Inhibitory Effect of Curcumin And Some Related Dietary Compounds on Tumor Promotion and Arachidonic Acid Metabolism in Mouse Skin." *Adv. Enzyme Regul* 31:385–396.

Huang et al. (1992) "Effect of dietary curcumin and ascorbyl palmitate on azoxymethanol–induced colonic epithelial cell proliferation and focal areas of dysplasia." *Cancer Letters* 64:117–121.
Huang et al. (1992) "Inhibitory effect of curcumin, an anti–inflammatory agent, on vascular smooth muscle cell proliferation." *Eur. J. Pharmacol* 221:381–384.
Huang et al. (1998) "Inhibitory Effect of Curcumin, Chlorogenic Acid, Caffeic Acid, and Ferulic Acid on Tumor Promotion in Mouse Skin by 12–O–Tetradecanoylphorbol–13–acetate." *Cancer Res.* 48:5941–5945.
Hussain et al. (1992) "Effect on curcumin on cholesterol gall–stone induction in mice." *Indian J. Med. Res.* 96:288–291.
Li et al. (1993) "Three inhibitors of type 1 human immunodeficiency virus long terminal repeat–directed gene expression and virus replication." *Proc. Natl. Acad. Sci. USA* 90:1839–1842.
Liu et al. "Inhibitory effects of curcumin on protein kinase C activity induced by 12–O–tetradacancol–phorbol–13–acetate in NIH 3T3 cells." *Carcinogenesis* 14:857–861.
Lu et al. (1992) "Inhibitory effect of curcumin on 12–O–tetradecanoylphorbol–13–acetate–induced increases in ornithine decarboxylase mRNA in mouse epidermis." *Carcinogenesis* 14(2):293–297.
Lutumski et al. (1974) "Wirkung Des Athanolextraktes Und Aktiver Substanzen Aus Curcuma Longa Auf Bakterien Und Pilze." *Planta Med* 26:9–19.
Mukudan et al. (1993) "Effect of turmeric and curcumin on BP–DNA adducts." *Carnogenesis* 14(3):493–496.
Ramprasad et al. (1957) "Observation on the Pharmacology of Curcuma Longa, Linn." *Ind. J. Phy and Pharm* 1:136–143.
Rao et al. (1982) "Anti–inflammatory activity of curcumin analogues." *Indian J. Med Res.* 75:574–578.
Saura et al. (1992) "Effect of ascorbic acid and curcmin on quercetin–induced nuclear DNA damage, lipid peroxidation and protein degradation." *Cancer Letters* 63:237–241.
Shih and Lin (1993) "Inhibition of 8–hydroxydeoxyguanosine formation by curcumin in mouse fibroblast cells." *Carcinogenesis* 14(4):709–712.
Soni et al. (1992) "Effect of Oral Curcumin Adminstration on Serium Peroxides and Cholesterol Levels in Human Volunteers." *Phys. Pharmacol* 36:273–275.
Soudamini et al. (1992) "Inhibition of Lipid Peroxidation and Cholesterol Levels in Mice by Curcumin." *Indian J. Phys. Pharmacol* 36:239–243.

\* cited by examiner

*Primary Examiner*—Christopher R. Tate
(74) *Attorney, Agent, or Firm*—Gary Baker; Quine Intellectual Property Law Group, P.C.

(57) ABSTRACT

Described are methods of promoting improvement of skin condition by administering a turmeric component and glycolic acid to a patient afflicted with a skin disorder.

12 Claims, No Drawings

COMPOSITIONS AND METHODS OF TREATMENT FOR SKIN CONDITIONS USING EXTRACTS OF TURMERIC

CROSS-REFERENCE TO RELATED APPLICATIONS

This application claims priority to U.S. Provisional Applications No. 60/149,219, filed Aug. 16, 1999.

FIELD OF TEE INVENTION

The present invention is directed to compositions comprising at least one component of turmeric (including, without limitation curcumin and turmerin) and one or more hydroxy acids, and methods of using these compositions to promote improvement of skin condition.

BACKGROUND OF THE INVENTION

*Curcuma longa* (Fam. Zingiberaccae) or Turmeric is one of the oldest herbs in Ayurveda materia medica, and has been used in Ayurveda medicine internally as a stomach, tonic and blood purifier, and topically in the prevention and treatment of skin diseases. Turmeric is a spicy plant that is a common ingredient in curry powder, usually in combination with other herbs such as cayenne, garlic, cumin and onion. Turmeric is also used as an additive in prepared mustard.

The significance of turmeric in medicine has changed considerably since the very recent discovery of the antioxidant properties of naturally occurring phenolic compounds. The same ground dried rhizome of *Curcuma longa*, which has been used for centuries as a spice, food preservative and a coloring agent, has been found to be a rich source of phenolic compounds or curcuminoids. There are three main curcuminoids recognized, i.e., curcumin (diferuloylmethane), demethoxy curcumin(p-hydroxycinnamoyl-feruloylmethane) and bis demethoxy-curcumin (p,p-dihydroxydicinnamoylmethane).

Curcuminoids have scientifically documented antioxidant, anti-inflammatory, anti-bacterial, anti-fungal, antiparasitic, anti-mutagen, anti-cancer and detoxification properties. Their potential use in the prevention of cancer and in the treatment of infection with human immunodeficiency virus (HIV) are the subject of intensive laboratory and clinical research. Curcuminoids are recognized for their broad biological activity and safety of use.

The pharmacokinetics involving the safety, toxicity, dose range, and biological properties of turmeric and its components, including curcumin and turmerin, are known, and the turmeric is readily available in various food stores.

Extensive in vitro and in vivo testing has shown that turmeric inhibits chemically-induced epidermal ornithine decarboxylase activity, epidermal DNA synthesis, and the promotion of skin tumors in mice (Conney A H et al., Adv. Enzyme Regul., 31:385–396, 1991; Huang M T et al., Cancer Res., 48:5941–5945, 1988; Lu Y P et al., Carcinogenesis, 14:293–297, 1993; Azuine M A, Bhide S V, Nutr Cancer, 17:77–83, 1992). Further studies suggest that turmeric also reduces arachidonic acid-induced rat paw and mouse skin edema and markedly inhibits epidermal lipoxygenase and cyclooxygenase activity in vitro (Rao T S et al., Indian J. Med. Res., 75:574–578, 1982; Conney A H et al., Adv. Enzyme Regul., 31:385–396, 1991; Huang M T et al., Cancer Res., 48:5941–5945, 1988). In humans, ingestion of turmeric has demonstrated a bacteriostatic or bacteriocidal effect against organisms involved in cholecystitis and has been used to treat biliary infections (Ramprasad C et al., Ind. J. Phys. and Pharm., 1:136–143, 1957; Lutumski J et al., Planta Med., 26:9–19, 1974). Topical application of a turmeric paste for the treatment of scabies has also shown good results (Charles V, Charles S X., Trop. Geogr. Med., 44:178–181, 1992).

It has been recently shown that curcumin decreased p24 antigen production in acutely or chronically infected cells with HIV-1, a paradigm of anti-viral activity (Li C J et al., Proc. Natl. Acad. Sci. USA, 90:1839–1842, 1993). Administration of curcumin in mice significantly reduced the scavenging of peroxides and other activated oxygen species, exhibiting its antioxidant property (Soudamini K K et al., Indian J. Phys. Pharmacol. 36:239–243, 1992). Oral administration of curcumin in human volunteers has been shown to significantly decrease the level of serum lipid peroxides (33%), increase HDL cholesterol (29%), and decrease total serum cholesterol (11.63%) (Soni K B, Kuttan R., Indian J. Phys. Pharmacol., 36:273–275, 1992).

The addition of turmeric to diet has been shown to inhibit azoxymethanol-induced colonic epithelial cell proliferation and focal areas of dysplasia (Huang M T et al., Cancer Letters, 64:117–121, 1992). It has also been shown to interfere with the formation of covalent carcinogen-DNA adducts (Mukudan M A et al., Cardnogenesis, 14:493–496, 1993).

Fat metabolism is likewise influenced by curcumin. It can render bile non-lithogenic in mice (Hussain M S et al., Indian J. Med. Rcs., 96:288–291, 1992). Curcumin can reduce the production of PMA-induced lipid peroxidation and 8-OH-deoxyguanosine formation in mouse fibroblast cells (Shih C-A, and Lin J-K, Carcinogenesis, 14:709–712, 1993).

Phosphorylation events can also be influenced by curcumin, as it has been reported that curcumin inhibits protein kinase C activity induced by 12-O-tetradecanoyl-phorbol-13-acetate in NIH 3T3 cells (Liu, J-Y, Lin, S-J, and Lin, J-K., Carcinogenesis, 14:857–861).

Curcumin inhibits the immune as well as the smooth muscle cell proliferation. Human peripheral blood mononuclear cells were inhibited in response to phytohemagglutinin and mixed lymphocyte reaction. Furthermore, curcumin inhibited the proliferation of rabbit vascular smooth muscle cells stimulated by fetal calf serum. Curcumin had a greater inhibitory effect on platelet derived growth factor-stimulated proliferation than on serum-stimulated proliferation (Huang H-C et al., Eur. J. Pharmacol., 221:381–384, 1992).

The anti-inflammatory properties of curcumin were shown to inhibit the 5-lipoxygenase activity in rat peritoneal neutrophils as well as the 12-lipoxygenase and the cyclooxygenase activities in human platelets (Ammon H P T et al, J. Ethopharmacol., 38:113–119, 1993). Curcumin had no significant effect on quercetin-induced nuclear DNA damage, lipid peroxidation and protein degradation and thus has the unique potential of acting as both pro- and antioxidants, depending on the redox state of their biological environment (Saura C et al., Cancer Letters, 63:237–241, 1992).

Alpha hydroxy acids, and more recently beta hydroxy acids, are commonly used as cosmetics to reduce wrinkles, spots and other signs of aging. Unfortunately, higher doses can cause undesirable side effects, including severe redness, swelling, burning, blistering, bleeding, rash, itching and skin discoloration. Alpha Hydroxy Acids for Skin Care, U.S. food and Drug Administration, FDA Consumer, March–April, 1998.

Most often used of the alpha hydroxy acids are glycolic acid and lactic acid, although several are useful alone or in combination with other alpha hydroxy acids.

What is needed is a composition and method of topically delivering alpha hydroxy acids and curcumin to the skin in doses that are highly effective without causing significant skin irritation.

SUMMARY OF THE INVENTION

The present invention is directed to compositions comprising at least one of the components of turmeric (such as curcumin or turmerin) and alpha hydroxy acid, and methods of using these compositions to promote improvement of skin condition. Various skin conditions can be treated in accordance with the present invention, including, but not limited to, conditions associated with scarring, unwanted pigmentation and aging of the skin. The present invention exhibits improved activity over the use of turmeric, curcumin or turmerin alone. Without limiting the scope of the invention, it is believed that the glycolic acid acts to enable the penetration.

After the administration of the combination of curcumin or turmerin and an alpha hydroxy acid, the skin is restored to a healthier and smoother appearance having improved texture and resilience. In accordance with the present invention, the skin disorders are preferably treated by administering the compositions of the present invention topically.

The present invention encompasses compositions comprising curcumin (and/or turmerin) and glycolic acid. In one embodiment, the amount of curcumin present is between approximately 0.1 and 20 µg/ml, preferably between approximately 1 and 5 µg/ml, more preferably between approximately 2 and 3 µg/ml. In another embodiment, the amount of glycolic acid present is between approximately 0.01 and 10%. The composition can further comprise one or more of the following compositions, turmerin, pantothenic acid, vitamin C, vitamin A, and salicylic acid.

The present invention further encompasses methods of promoting healing of a scar, treating skin pigmentation and treating skin conditions associated with aging in a patient, comprising topically administering a composition comprising an effective amount of curcumin and glycolic acid to said patient.

Also encompassed by the present invention are methods wherein the amount of curcumin administered is between approximately 0.1 µg/ml and 20 µg/ml, and/or wherein the amount of glycolic acid administered is between approximately 0.01 and 10%.

DETAILED DESCRIPTION OF THE INVENTION

The present invention is directed to compositions comprising one or more components of turmeric (including, without limitation, curcumin and turmerin) and alpha hydroxy acid, and methods of using these compositions to promote improvement of skin condition. Various skin conditions can be treated in accordance with the present invention, including, but not limited to, conditions associated with scarring, unwanted pigmentation and aging of the skin.

This section is divided into four parts: I. General Application Of The Compositions Of The Present Invention, II. Turmeric Components, III. Indications For The Use Of Compounds Of The Present Invention, And IV. Formulation Of Compositions of The Present Invention.

I. General Description of the Compositions of the Present Invention

An effective amount of curcumin or turmerin and alpha hydroxy acid is administered to a host who is to be treated. An effective amount is a quantity of curcumin or turmerin and alpha or beta hydroxy acid which produces the desired effect, e.g., which treats (e.g., ameliorates) the skin disorder. The curcumin is generally administered in a range of from about 0.1 to 40 µg per day, preferably about 2 to 6 µg per day. In one treatment regime, about 2 to 3 µg of curcumin is administered per day until the condition is ameliorated.

The turmerin is generally administered in a range of from about 0.1 to 20 µg per day, preferably about 1 to 3 µg per day.

Turmeric is a member of the family Zingiberaceae. It is generally obtained from the rhizome of the plant Curcuma loga. Turmeric can be obtained from various sources, including commercially available sources. Curcumin, turmerin and other extracts of Turmeric can also be synthesized or obtained by one of ordinary skill in the art by reference to literature on the subject. Acros Organics, Fluka and Sigma-Aldrich all sell a synthetically produced curcumin.

Various forms of turmeric, including fresh, powdered, liquid juice, pulp, or resin, can be utilized to provide compositions such as curcumin and turmerin for use in accordance with the present invention.

The present invention is directed to the use of components of turmeric (including, without limitation, curcumin and turmerin) and glycolic acid to promote resolution of scars, skin pigmentation and aging skin conditions. The use of curcumin or turmerin and glycolic acid at the site of the skin condition by topical application will promote more rapid resolution of these skin conditions.

Turmeric components in combination with alpha hydroxy acids have improved antineoplastic, antioxidant, antibacterial and anti-inflammatory properties when applied topically. Without limiting the invention to any particular mechanism, it is believed that, when the turmeric component(s) are combined with alpha hydroxy acids, the effective concentration of the turmerin and curcumin provides a more active composition for treatment of scars, pigmentation and aging skin. It is believed that, when combined with alpha hydroxy acid, the component(s) of turmeric (in particular curcumin and turmerin) are able to penetrate the skin and have a pronounced effect on the skin being treated that would not be achieved in the absence of alpha hydroxy acid.

Alpha- and beta-hydroxy acids ranging from $C_2$–$C_{30}$ are also suitable for the present invention. The beta-hydroxycarboxylic acids are primarily exemplified by salicylic acid and C.sub.1–C.sub.30 ester and salt derivatives. Examples of suitable alpha-hydroxycarboxylic acids include but are not limited to:

alpha hydroxy acetic acid (h1h3glycolic acid)
alpha hydroxybenzeneacetic acid (mandelic acid)
alpha hydroxypropionic acid (lactic acid)
alpha hydroxybutanoic acid
alpha hydroxyhexanoic acid
alpha hydroxyoctanoic acid (alpha hydroxycaprylic acid)
alpha hydroxynonanoic acid
alpha hydroxydecanoic acid
alpha hydroxyundecanoic acid
alpha hydroxydodecanoic acid (alpha hydroxylauric acid)
alpha hydroxytetradecanoic acid
alpha hydrocyhexadecanoic acid
alpha hydroxyoctadecanoic acid
alpha hydroxyoctaeicosanoic acid;

dicarboxylic alpha hydroxy acids;
dihydroxybutanedioic acid (tartaric acid)
2-hydroxybutanedioic acid (malic acid)
2-hydroxy propanedioic acid
2-hydroxy hexanedioic acid
2-hydroxy octanedioic acid
2-hydroxy decanedioic acid
2-hydroxy dodecanedioic acid
2-hydroxy myristicdioic acid
2-hydroxy palmiticdioic acid
Tricarboxylic alpha hydroxy acid;
2-hydroxy-1,2,3,-propanetricarboxylic acid (citric acid)
1-hydroxy-1,2,3-propanetricarboxylic acid (isocitric acid) and mixtures thereof.

hydroxycarboxylic acids (e.g. potassium, sodium, ammonium, triethanolammonium salts) are also meant to be included within the term "alpha- and beta-hydroxycarboxylic acid". Depending on the pH of the composition, a mixture of the salt and the acid may be present.

The preferred alpha hydroxycarboxylic acids are monocarboxylic acids, in order to improve skin penetration and efficacy.

Even more preferably, the hydroxy acid is chosen from lactic acid, $H_2H_4$glycolic acid, mandelic acid, and mixtures thereof to optimize the efficacy of compositions by increasing percutaneous absorption. Most preferred is the L-form of an alpha hydroxycarboxylic acid.

While many routes of intake of the compositions of the present invention are encompassed, there are clear benefits to using the compositions topically, including that of ease of delivery and specific treatment of effected sites.

II. Turmeric Components

Turmeric contains curcumin (water insoluble components) and turmerin (water-soluble components). "Turmeric components" shall herein refer to turmerin and curcumin.

A. Curcumin Consists of
  Curcumin I (Diferuloylmethane)
  Curcumin II (Feruloyl-P-HydroxyCinnamoylmethane)
  Curcumin III {Bis-(P-Hydroxycinnamoyl)methane}

Curcumin is able to scavenge superoxide radicals. See, Free radical scavenging activity of Curcumoids. Sreejayan N, Rao Mn, Arzneimittelforschung Febuary 1996; 46(2):169–71. Curcumin is scavenger of Nitric Oxide. Sreejayan, Rao MN, Nitric Oxide scavenging by Curcumoids. J Pharm Pharmacol January 1997; 49(1): 105–7.

Curcumin is a potent inhibitor of Arachidonic Acid inducing inflammation Srinivas L, Shalini V K, Shylaya M., Turmerin: a water soluble antioxidant peptide from Turmeric. Arch Biochem Biophys February 1992 peptide from Turmeric. Arch Biochem Biophys Feb. 1, 1992;292(2):617–23. Curcumin is considered to be an antioxidant and anti-inflammation agent. Concise Encyclopedia Chemistry, Walter de Gruyter Berlon—New York 1994—Page 1161—Second edition.

B. Turmerin Consists of
  Non-cyclic peptide and 3 Methionine residues A 24 Kd protein that is water-soluble.
  Chlorogenic Acid
  Caffeoic Acid
  Ferulic Acid
  Water soluble lipid The non-cyclic 5 Kd peptide is water-soluble and is believed to be an anti-oxidant agent. Anti-oxidant activity of Curcumin and related compounds, Sharma Biochemical Pharmacology, Vol. 25.pp1881–1882. Pergamon Press 1976.

There are three Methionine residues present in Turmerin. Anti-oxidant activity of Curcumin and related compounds. Sharma Biochemical Pharmacology, Vol. 25.pp1881–1882. Pergamon Press 1976. Turmerin also contains water-soluble protein that is an anti-oxidant protein.

II. Indications for the Use of Compounds of the Present Invention

Curcumin and glycolic acid mixture can be formulated into conventional topical formulations for the following indications:

A. Scar Treatment

Annually there are millions of surgical procedures, million of cesarean sections, burns and injury-related visits to emergency rooms and trauma center (not including minor cut at home especially with children), all of which may leave a scar.

There are many factors involved in scar formation, such as age, location and size of wound, poor nutrition, genetics or infection and re-injury of the wound site.

Curcumin, turmerin and glycolic acid have proven to be a powerful combination that can stop the formation of a scar from a healing wound (depending on the size of the wound) or make a scar look smoother and softer (including hypertrophic and keloid Scars).

A typical scar starts to form while the wound is healing and remains after the healing is completed. The appearances of scar depend on how fast the healing process is completed.

With its abilities to support cells growth and regenerate new tissue, the compositions and methods of the present invention can be used to make a new scar reduce in size or color or disappear, or improve the appearances of an older scar.

Scars that benefit from this treatment include, without limitation, any damage to the skin that prevents the skin from returning to its pre-damaged appearance after healing. Some examples include the results of cuts, surgery, acne, and rashes.

B. Aging Skin and Dried Skin

In the cosmetics market, people excessive amounts of money to treat aging and unhealthy skin.

Today, more and more pharmaceutical companies are researching to find better treatments for aging skin, especially from unexplored herbal resources.

Free radicals and oxidants have long been believed to have a hand in aging the skin and causing dried/unhealthy skin. Free radicals are a main factor in wrinkling of aging skin cells and even are suspected of having a carcinogenic effect.

Oxidants can oxidize essential fatty acid such as arachidonic acid and other essential fatty acids that are needed for skin cells to stay healthy. Lack of arachidonic acid can cause scaly dried skin and slow growth of skin cells. Arachidonic Acid, Harper's Review of Biochemistry, Lange Medical Publications, Los Altos, Calif. (1981), pages 187–188, 209, 213.

Turmeric components can prevent the oxidizing process of essential fatty acids to protect the healthy and smooth appearance of the skin surface.

Due to the free radical scavenging activity of curcumin, and the penetrating qualities of alpha and beta hydroxy acids, components of turmeric can be used with the acids topically to treat wrinkled and aging skin effectively.

Additionally, methionine is an essential component to keep skin cell growing normally without any damages that may lead to cell destruction. Salicylic Acid, Concise Encyclopedia Chemistry by Walter de Gruyter Berlin—New York 1994—Page 645—Second edition.

C. Skin Pigmentation

Due to the side affects of medications or sun exposure, many women, especially from Asia and South America, develop undesirable skin pigmentation on their face and body.

Curcumin has proved to be an anti-protein kinase that can help skin cell and hair to return to normal pigmentation. Women who have pigmentation may benefit from using turmeric instead of more invasive procedures, such as Laser skin resurfacing or skin peeling procedures. And at the same time, they can maintain healthy appearance of the skin without costly makeup.

IV. Formulation of Compositions of the Present Invention

The compositions of the present invention can be administered alone, or they can be mixed with a pharmaceutically or cosmetically acceptable carrier or diluent.

Alpha and beta hydroxy acids, including, but not limited to, glycolic acid and salicylic acid, can be used in relatively high concentrations for all compositions and methods of the present invention. However, care must be taken to ensure the patient will tolerate higher concentrations. A gradual approach to raising the concentration of glycolic acid is preferred to avoid adverse reactions in some patients. In compositions of the present invention, an alpha hydroxy acid concentration of between approximately 0.01 $\mu$g/ml and 20 $\mu$g/ml is contemplated, preferably between approximately 0.1 $\mu$g/ml and 10 $\mu$g/ml, more preferably between approximately 1 $\mu$g/ml and 5 $\mu$g/ml.

A detailed description of preferred proportions of the components of turmeric and their preparation is provided in U.S. Pat. No. 5,861,415, hereby incorporated by reference. Turmeric can be formulated as a topical preparation by bringing it into a suitable dose form, e.g., together with an excipient or auxiliary, and, if desired, with one or more further active compounds. The preparations can be utilized in both human and veterinary medicine. Suitable excipient include, e.g., organic and inorganic substances which are appropriate for enteral, parenteral, or oral administration, e.g., water, saline, buffers, vegetable oils, mineral oils, benzyl alcohol, cyclodextrin, hydroxypropylcyclodextrin (especially beta-type), polyethylene glycols, glycerol triacetate and other fatty acid glycerides, gelatin, soya lecithin, carbohydrates such as lactose or starch or other sugars, magnesium stearate, talc or cellulose. The preparations can be sterilized and/or contain additives, such as preservatives or stabilizers. Turmeric can be formulated with various oils, including coconut, sunflower, mustard, almond, sesame, safflower, or peanut.

Curcumin, and/or turmerin, and alpha or beta hydroxy acids can be formulated with various active agents, e.g., vitamin E, tocopheryl acetate, calcium. Turmeric can also be formulated with other herbs and plants, depending on the desired purpose and effect. These herbs and plants include, ginger, garlic, fenugreek, guava leaves, *Aquilaria agallocha, Ficus racemosa, Saraca asoka, Trigionell foenum-graecum, Curcuma aromatica, Meriandra bengalensis, Zanthoxylum budrunga, Withania somnifera, Crocus sativus, Saussurea lappa*. And for haircase: *Eclipta alba, Bacopa monnieri, Sida retusa, Indigofera tinctoria, Cardiospermum halicacabum, Hibiscus rosasinensis*. Other plants and herbs include those mentioned in various text and publications, e.g., E S Ayensu, Medicinal Plants of West Africa, Reference Publications, Algonac, Mich. (1978); P. Back, The Illustrated Herbal 1987, Hamlyn Publishers, distributed by Octopus Books, Printed in Hong Kong by Mandarin, ISBN 0-600 553 361; F. Bianchini and F. Corbetta, The Fruits of the Earth, translated from Italian by A. Mancinelli, Bloomsbury Books, London, ISBN 1-870630-10-6; H. M. Burkill, The Useful plants of West Tropical Africa, Ed. 2, V. I, Royal Botanic Gardens Kew, ISBN 0-947643-01-X (1985); L. Boulos, Medicinal Plants of North Africa, Reference Publications Inc., Algonac, Mich. (1983); and N. C. Shah, Herbal folk medicines in Northern India, J. Ethnopharm, 6:294–295 (1982). The turmeric can also be formulated with components as described in CN 1098926 and JP 7309713.

Curcumin, and/or turmerin, and alpha or beta hydroxy acid can also be formulated into topical preparations. Carriers useful in formulating the preparations are commonly used pharmaceutically acceptable non-toxic carriers. A preferred preparation comprises a turmeric component, glycolic acid, a cream base, vitamins C and E, dimethicone, and salicylic acid. Other ingredients that can be combined in a topical preparation include, sodium lauryl sulfate, oleanic acid, linoleamide DEA, glycol stearate, stearic acid, sodium hydroide, trisodium EDTA, tetrasodium EDTA, alcohols, polyethylene glycols, fragrances, preservatives, deionized water, dimethicone, glycerin, antibacterials, and other ingredients that the skilled worker would know.

The turmeric component and alpha or beta hydroxy acid can also be co-administered with other active agents to achieve synergistic effects. For example, the turmeric can be co-administered with an antibiotic for the treatment of any of the above-mentioned disorders. Other active agents include, e.g., antioxidants, such as, but not limited to, Vitamins A and E, anticarcinogens, antiinflammatory agents, hormones and hormone antagonists, antibiotics and other antibacterial agents, and other medically useful composition such as those identified in, e.g., Remington's Pharmaceutical Sciences, Eighteenth Edition, Mack Publishing Company, 1990.

The following formulations are merely examples of preparation of the compositions of the present invention, and in no way limit the scope of the invention:

1. Scar Treatment

For topical treatment of scars turmeric components can be formulated in conventional cream such as, without limiting the scope of the invention, the following approximate mixture: 1 part of cream and 2 parts of solution extracted as described in Example 1, with approximately 0.01 to 10% v/v of Glycolic Acid. An alpha hydroxy acid concentration of between approximately 0.01% and 70% is contemplated, preferably between approximately 1% and 20%, more preferably between approximately 5% and 10%.

In a specific embodiment of the invention, the formulation includes turmeric component(s), Vitamin B, Vitamin E, Glycolic acid, Salicylic acid and Dimethicone in a conventional cream base.

2. Dry, Unhealthy Skin, Use as a Moisturizer

Turmerin can be formulated into conventional cream plus Vitamin C and/or Vitamin E (1–10%), Vitamin B Pantothenic Acid (1–5%), Glycolic Acid (1–10%) and Salicylic Acid (1–10%) to be used as moisturizer.

1. Vitamin C (Ascorbic Acid) is an anti-oxidant that inhibits the oxidation by oxygen radicals. Vitamin C, Ascorbic Acid, Concise Encyclopedia Chemistry, Walter de Gruyter Berlon—New York 1994—Page 1161—Second edition.

Vitamin B-Pantothenic Acid has been used to treat membrane mucous inflammation. Vitamin B, Pantothenic Acid. Concise Encyclopedia Chemistry Walter de Gruyter Berlon—New York 1994, Page 775, Second edition.

Glycolic Acid (Alpha Hydroxy Acid) aids in dead skin removal. In one embodiment of the present invention, the pH of a mixture containing glycolic acid is greater than 4.0. Alpha Hydroxy Acids for Skin Care. FDA consumer, March–April 1998.

Salicylic Acid (Beta Hydroxy Acid) has been shown to aid in dead skin removal, Alpha Hydroxy Acids for Skin Care. FDA Consumer, March–April 1998, and to have a keratolytic effect that is useful for skin treatment. Salicylic Acid, Concise Encyclopedia Chemistry Second edition, Walter de Gruyter, Berlin—New York 1994, Page 962 et seq.

Turmeric components (Curcumin and Turmerin) can be formulated into cream plus Vitamin C, Vitamin B, Glycolic Acid and Salicylic Acid to treat dry and unhealthy skin. In a specific embodiment of the present invention, turmeric component(s) can be combined with these compositions in the following concentrations: Vitamin C (1–10%), Vitamin B (1–15%), Glycolic Acid (1–10%) and Salicylic Acid (1–10%).

An alpha hydroxy acid concentration of between approximately 0.01% and 70% is contemplated, preferably between approximately 1% and 20%, more preferably between approximately 5% and 10%.

In a specific embodiment, the following composition is useful for treating aging and dry skin: Turmerin, Glycolic acid, Salicylic Acid, Vitamin E, Vitamin B, lecithin and a source of Sun Protection Factor of approximately 15.

3. Aging Skin

In one particular embodiment of the present invention an anti wrinkle formulation for aging skin is contemplated that encompasses the components described above for use on dry, unhealthy skin, and also encompasses the use of vitamin A. In a specific embodiment, the vitamin A is present in the formulation in a concentration of approximately 2%.

4. Skin Pigmentation

In one embodiment, for treating skin pigmentation, turmeric component(s) can be formulated (1:1) in a cream based plus 1–10% glycolic acid and 1–10% salicylic acid to treat skin pigmentation.

An alpha hydroxy acid concentration of between approximately 0.01% and 70% is contemplated, preferably between approximately 1% and 20%, more preferably between approximately 5% and 10%.

In a specific embodiment, the present composition is seful for treating skin pigmentation: Turmerin, itamin E, Vitamin B, Glycolic Acid, Dimethicone, PF 15 plus conventional cream base.

III. Topical Treatment

1. Scar Treatment

These suggested formulations, as well as others based on the teachings herein, can be applied directly over the open wound at the beginning with out the use of antibiotic. Although the formulations of the present invention can be used earlier and are beneficial if first applied later, it is preferable to begin treating the wound from 2 to 7 days after injury. The wound starts to heal with treatment and the area around the wound dries quickly.

Continue to apply the cream onto the scar for as long as improvements continue, which will depend upon the size and type of the scar, to help reduce the size and appearance of the scar. With a newly form scar, improvement can occur as early as 1 month to 2 month of daily treatment. With small sized injuries and new scars, the formulations of the present invention can make the scar not noticable.

2. Skin Pigmentation

In one embodiment of the present invention, the formulations for treatment of either skin pigmentation or scars are applied directly onto the effected area a minimum of twice a day.

Results of treatment can show improvement in skin pigmentation as early as two weeks after treatment is initiated. However, treatment can continue as long as the condition continues to improve.

EXPERIMENTAL

Example 1

Preparation of Turmeric Components

Components of turmeric can be isolated in a variety of ways. The following is one method that was used to obtain curcumin and turmerin.

First, the skin of the turmeric rhizome was removed. The turmeric was then sliced into small thin pieces. One gram of dried Turmeric was added to 10 mL of hot water or 20% Ethanol (V/V). The mixture was placed in a beaker and covered to protect light sensitive components. The contents of the beaker were mixed and incubated at room temperature for 24 hours. Then, a small pore size filter was used to remove debris from the solution. Next, the mixture was centrifuged at low speed to remove small particles, then at high speed to separate curcumin and turmerin depending on formulation and purposes. The curcumin and turmerin were then carefully isolated. Although the amounts of products of extraction vary slightly, guidance from analysis and from the literature support that approximately 1–5% of turmeric is curcumin and 0.1% is turmerin. Srinivas, L., et. al., Turmerin: A Water Soluble Antioxidant Peptide from Turmeric [Curcuma longa], Archives of Biochemistry and Biophysics, 292:617 (1992). This reference also gives a detailed description of the biochemical features of turmerin.

Example 2

The formulation described below was prepared and applied daily to several types of scars.

Scar Treatment Formulation

Turmerin obtained from turmeric as described in Example 1

2.0% Glycolic Acid 3,000 Unit Vitamin E 0.5% Panthenol (Vitamin B)

Dimethicone

Cream base

Normal Flat Scar

The scar was located on the leg. It was caused by an accident. The treatment commenced three months following the accident. Treatment proceeded for approximately three and one half months. By the end of treatment, the scar had disappeared.

Hypertrophic Scar

These scars were located on the joints at elbow and wrist. The scars were the result of surgery. The treatment began eight months following the surgery. Treatment continued for four months. As the treatment progressed, the scar flattened out and became smooth. At the completion of treatment the scar was no longer noticeable.

Hypertrophic Scar

This scar was located on the individual's knee. It was caused by an accident. In this case, treatment began immediately after the injury had healed, and lasted for two and one half months. At this point, treatment is ongoing. Thus far, the treatment has rendered the scar smooth and the scar tissue color has begun to fade to match the undamaged skin.

Skin Care Moisturizer and Aging Formulation

Turmeric components obtained as described in Example (containing curcumin and turmerin)

2.0% Glycolic acid 0.5% Panthenol (Vitamin B)

3,000 Unit Vitamin E

Cream base

Dimethicone

A group of 20 people used the above mixture twice a day. Eighty-percent of the users experienced improvement in skin condition (Skin looked younger, more resilient, and firmer). Ten percent of the users experienced mildly irritated skin, characterized by itching, and discontinued use. Another ten percent saw no change in skin condition.

Skin Pigmentation Formulation

Turmeric components obtained as described in Example 1.

2.0% Glycolic acid 0.5% Penthenol (Vitamin B)

3,000 Unit Vitamin E

Cream base

Dimethicone

Of the 40 users of the above mixture, on a twice daily basis, seventy percent experienced complete resolution of pigmented skin and have not experienced new pigmentation. An additional ten percent showed some fading of pigmented skin. The final twenty percent stopped after developing mild skin irritation characterized by itching. In all cases, the skin irritation is believed to be caused by the glycolic acid. This itching can be eliminated in most cases by careful monitoring and reduction of glycolic acid percent levels in the treatment. Alternatively, the pH of the composition can be adjusted to be more compatible with topical applications.

The preceding examples can be repeated with similar success by substituting the generically or specifically described reactants and/or operating conditions of this invention for those used in the preceding examples.

The entire disclosure of all applications, patents and publications, cited above, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A composition comprising a turmeric component and a hydroxy acid, wherein the turmeric component comprises turmerin at a concentration between about 0.1 $\mu$g/ml and approximately 20 $\mu$g/ml, or curcumin at a concentration between about 1 $\mu$g/ml and approximately 20 $\mu$g/ml.

2. The composition of claim 1, wherein said turmeric component is curcumin.

3. The composition of claim 1, wherein said hydroxy acid is glycolic acid.

4. The composition of claim 3, wherein the amount of said glycolic acid present is between approximately 0.01 and 10%.

5. The composition of claim 1, wherein said turmeric component is turmerin.

6. The composition of claim 1, further comprising pantothenic acid.

7. The composition of claim 1, further comprising vitamin C.

8. The composition of claim 1, further comprising salicylic acid.

9. A method of promoting healing of a scar in a patient, comprising topically administering a composition comprising an effective amount of a turmeric component and glycolic acid to said patient, wherein the amount of said turmeric component administered comprises turmerin at a concentration between approximately 0.1 $\mu$g/ml and approximately 20 $\mu$g/ml, or curcumin at a concentration between approximately 1 $\mu$g/ml and approximately 20 $\mu$g/ml.

10. A method of treating skin pigmentation in a patient, comprising administering topically an effective amount of a composition comprising a turmeric component and glycolic acid to said patient, wherein the amount of said turmeric component administered comprises turmerin at a concentration between approximately 0.1 $\mu$g/ml and approximately 20 $\mu$g/ml, or curcumin at a concentration between approximately 1 $\mu$g/ml and approximately 20 $\mu$g/ml.

11. The method of claim 9 or 10, wherein said hydroxy acid is glycolic acid.

12. A composition comprising curcumin at a concentration between approximately 1 $\mu$g/ml and approximately 20 $\mu$g/ml, and an alpha hydroxy acid.

\* \* \* \* \*